United States Patent [19]
Berman et al.

[11] Patent Number: 5,458,648
[45] Date of Patent: Oct. 17, 1995

[54] GREAT TOE JOINT IMPLANT AND METHOD OF IMPLANTATION

[75] Inventors: James Berman, San Diego; Michael J. Durbin, Pleasant Hill; Daniel E. E. Hayes, Jr., Sacramento; Glynnis E. Stone, Cardiff, all of Calif.

[73] Assignee: Kinetikos Medical, Inc., San Diego, Calif.

[21] Appl. No.: 240,343

[22] Filed: May 10, 1994

Related U.S. Application Data

[63] Continuation-in-part of Ser. No. 201,104, Feb. 24, 1994, abandoned.

[51] Int. Cl.⁶ ..................................................... A61F 2/42
[52] U.S. Cl. ......................................................... 623/21
[58] Field of Search ........................................ 623/18, 21

[56] References Cited

U.S. PATENT DOCUMENTS

| | | | |
|---|---|---|---|
| 4,470,158 | 9/1984 | Pappas et al. | 623/18 |
| 4,908,031 | 3/1990 | Frisch | 623/21 |
| 5,037,440 | 8/1991 | Koenig | 623/21 |
| 5,314,486 | 5/1994 | Zang et al. | 623/21 |

FOREIGN PATENT DOCUMENTS

| | | | |
|---|---|---|---|
| 2645735 | 10/1990 | France | 623/21 |

Primary Examiner—David Isabella
Assistant Examiner—Laura Fossum
Attorney, Agent, or Firm—Townsend and Townsend and Crew

[57] ABSTRACT

A nonconstrained, total great toe joint implant for the metatarsophalangeal joint made of a first component with a convex, partially spherical surface ending in a rear surface from which a longitudinally asymmetric implantation stem projects and having a flange on the dorsal side of the implant which extends the convex surface past the rear surface. The rear surface is inclined 10° relative to a normal plane which intersects this surface. The metatarsal bone is resected accordingly. The phalangeal implant component is made of a base with a stem for placement in a bone cavity, projecting from a rear side thereof and having a low-friction, concavely curved insert affixed to the base which slidably engages and cooperates with the convex surface of the metatarsal implant component. The base has an outline corresponding approximately to the outline of the resected surface on the phalangeal bone to eliminate bone-overhang and bony overgrowth that may result from such an overhang and which can compromise the proper functioning of the implant. The metatarsal implant component has right foot and left foot configurations resulting from the relative positioning and orientation of the asymmetrically shaped stem projecting from the rear surface thereof.

8 Claims, 4 Drawing Sheets

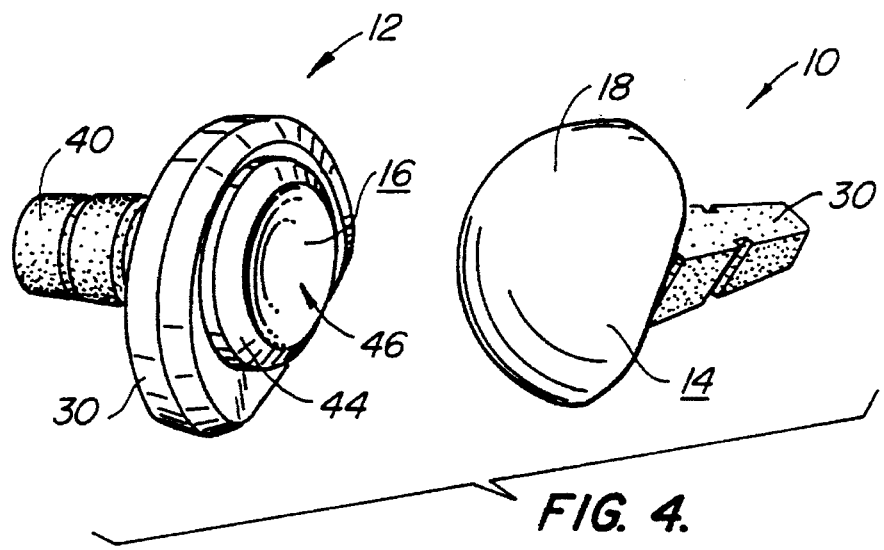
FIG. 4.
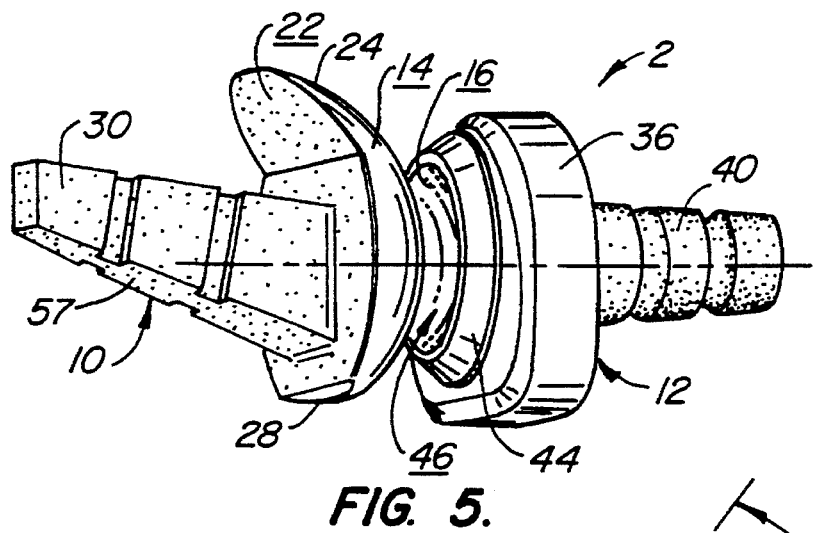
FIG. 5.
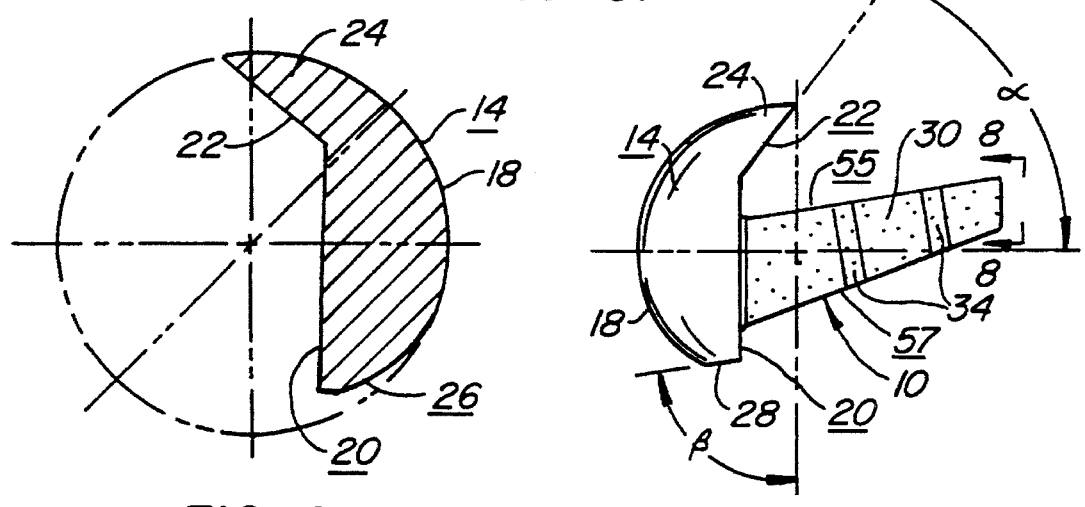
FIG. 6.
FIG. 7.
FIG. 8.

GREAT TOE JOINT IMPLANT AND METHOD OF IMPLANTATION

RELATED APPLICATIONS

This application is a continuation-in-part application of the patent application of the inventors bearing Ser. No. 08/201,104, filed Feb. 24, 1994, now abandoned.

BACKGROUND OF THE INVENTION

The present invention relates to a nonconstrained prosthetic implant for the replacement of metatarsophalangeal joints.

The replacement of degenerated natural joints with man-made prosthetic replacements is well known, including the replacement of the metatarsophalangeal joint (MPJ) of the great toe. One such replacement, to which the present invention relates, uses a two-piece, nonconstrained prosthesis to replace the first MPJ where the metatarsal head is resected and replaced with a metal component and the proximal phalanx is resected and replaced with a metal-backed polyethylene component.

The early implants for the great toe were hemiarthroplasty devices, where only one side of the joint was replaced-either the metatarsal head or the proximal phalanx. As early as the 1950's, one Swanson developed a metal replacement for the metatarsal head, fixed with an intramedullary stem. The procedure was deemed unsuccessful, and failure was attributed to resorption of bone around the stem. In the mid-1960's, Swanson became aware of a medical-grade silicone developed by Dow Corning. First, he tried replacing the metatarsal head with the material, but because of high shear and compressive loads across the first MPJ during gait, the prosthesis failed. Because of the failures incurred by using a hemiarthroplasty on the metatarsal side, he turned his attention to the proximal phalanx. He designed a silicone implant having an intramedullary stem and proximal portion that acted as a spacer, replacing the bone which is resected in a Keller procedure. Because the implant was only acting as a spacer, it lacked full functional motion and caused severe reactions of the surrounding bone due to debris thought to be generated by wear between the implant and metatarsal head.

In the 1970's, a double-stem hinged implant similar to one for the metacarpophalangeal joint (base of the finger) was developed using a new High Performance Silastic Elastomer. Various forms of such constrained, silastic implants have been in use ever since, and they have been relatively successful. Pain relief is obtained in almost all cases, patients have the ability to walk, and functional scores have been shown to increase. While the range of motion has increased compared to the other available options (fusion, Keller procedure), a fully functional toe has not been the result. Often, due to the constraining nature of the devices, the implant pistons in and out of the medullary canal, causing debris formation and synovitis. In view of the recent silicone breast implant scare, there is now much concern about the use of silicone-based implants in the hand and foot. Thus, the two-piece metal on poly designs that have worked so well in the hip and knee areas are now being considered by many for MPJ replacements.

The somewhat unconstrained implants on the market today have a metatarsal component (generally cobalt chromium alloy) with a convex articulating surface that mates with a concave medical-grade ultra high molecular weight polyethylene (UHMWPE) metal-backed (generally titanium alloy) phalangeal component. Both components utilize an intramedullary stem for stability and fixation purposes.

A great toe replacement, developed by one Richard Koenig, DPM, and marketed under the trademark Biomet, utilizes a medial surgical approach to address the plantar articulation of the sesamoids with the plantar surface of the metatarsal head. The metatarsal component wraps around the dorsal to plantar aspect of the metatarsal head. This replacement, with its somewhat difficult surgical implantation technique, was introduced in the late 1980's. The dorsal flange of this replacement allows a normal range of dorsiflexion, but may cause interfered motion of the sesamoid/plantar metatarsal articulation. While there is unconstrained motion from dorsal to plantar, the motion of this implant is in fact semi-constrained because of the flatter radius of curvature medial to lateral, which inhibits the motion.

In the early 1990's, podiatrist Kerry Zang developed a simpler replacement which is available from MicroAire Surgical Instruments, Inc. of Valencia, Calif., under the trademark Bio-Action. Neutral cuts (generally perpendicular to the long axis of the bone) are made on both the phalanx and metatarsal head. The metatarsal head is replaced with less than a hemisphere of a somewhat spherical surface, while the phalangeal base is covered by a circular metal-backed polyethylene insert. The range of motion during walking is limited due to the absence of a dorsal flange; however, the sesamoid/metatarsal articulation is relatively undisturbed. This implant, due to its generally spherical surface, is unconstrained. Its medial to lateral alignment is maintained by the soft tissue and not by the implant design.

In early 1993, another great toe implant became available from Acumed. This implant combines some of the positive aspects of the two previously discussed implants—the dorsal flange of the Biomet-Koenig implant with the noninvasive plantar aspect of the Bio-Action implant. The Acumed toe is similar to the Koenig implant because it is also semi-constrained due to a flatter radius limiting the motion in the medial to lateral direction. Both the Acumed and Biomet toes require a proper, perpendicular alignment of the neutral cut with the convex surface of the metatarsal implant component.

SUMMARY OF THE INVENTION

The great toe implant of the present invention uniquely combines a number of positive design features to provide a totally unconstrained implant having an optimal range of motion dorsally without interference of the plantar metatarsal/sesamoid articulation. The implant procedure employs a 10° resection relative to the distal surface or neutral plane of the metatarsal head. This allows for uninterrupted motion of the metatarsal/sesamoid articulation, requires minimal bone resection, and rotates the articulating surface of the metatarsal head 10° dorsally to provide a more normal range of motion during gait. In combination, the somewhat spherical surface dorsally provides for unconstrained motion medial to lateral as well as plantar to distal.

Because of the sphericity of the articulating surface, the initial resection is not alignment sensitive (medial to lateral), as are some of the known, semi-constrained implants mentioned above. While known implants and the implant of the present invention have intramedullary stems to provide stability and fixation, the intramedullary stems of the implant of the present invention are uniquely adapted to achieve maximum stability and optimal fixation. The plantar surface of the metatarsal stem is inclined to follow the anatomic inclination of the metatarsal shaft, and the stem is alignment insensitive by providing for the anatomic right and left angles of the metatarsal shaft. The stem is squared, providing additional torsional stability (the dorsal flange also prevents axial rotation of the component). Grooves are further provided on both the metatarsal and phalangeal stems to provide for bony ingrowth or cement interdigitation. The grooves on the phalangeal component prevent axial rotation and inhibit pull-out of the stem itself.

BRIEF DESCRIPTION OF THE DRAWINGS

FIG. 4 is a perspective, side elevational view showing the metatarsal and the phalangeal implant components of the present invention;

FIG. 5 is a perspective view showing the metatarsal and phalangeal components of the present invention from the other side;

FIG. 6 is a schematic, cross-sectional view showing a head portion of the metatarsal implant component;

FIG. 7 is a side elevational view of the metatarsal implant component;

FIG. 8 is an end view taken along line 8—8 of FIG. 7;

DESCRIPTION OF THE PREFERRED EMBODIMENTS

Figure 1:
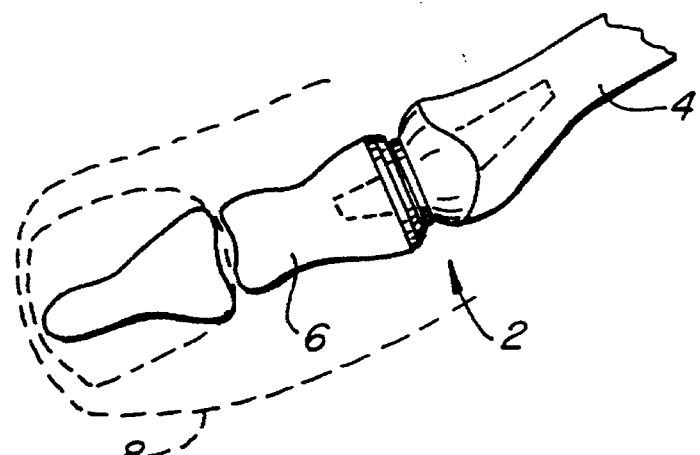
FIG. 1 is a schematic, fragmentary plan view of a great toe (shown in phantom lines) and its skeletal structure and illustrates the implant of the present invention forming a nonconstrained joint between the metatarsal and phalangeal bones.
Figure 2:
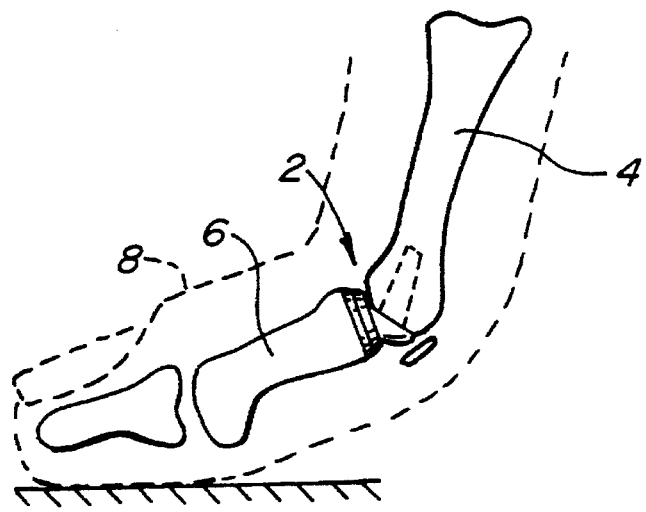
FIG. 2 is a fragmentary, side elevational view of a great toe (shown in phantom lines) and illustrates the toe in dorsiflexion.
Figure 3:
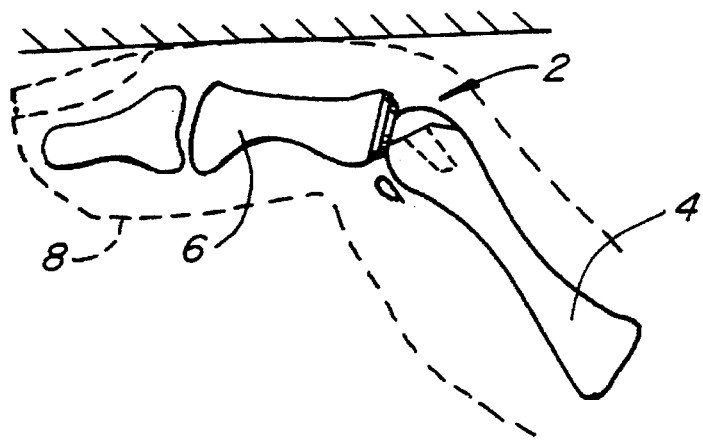
FIG. 3 is a schematic side elevational view similar to FIG. 2 illustrating the toe in plantarflexion.
Figure 9:
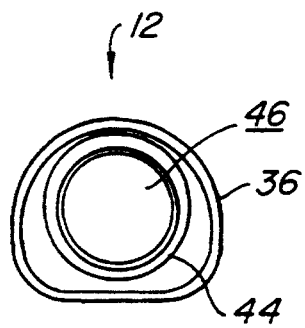
FIG. 9 is a front elevational view of the phalangeal implant component of the present invention.
Figure 10:
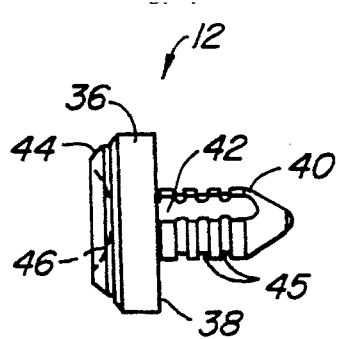
FIG. 10 is a side elevational view of the phalangeal implant component.

Referring to FIGS. 1–3, a great toe implant 2 constructed in accordance with the present invention forms a nonconstrained joint between the metatarsal bone 4 and phalangeal bone 6 of a great or big toe 8 so that the toe can be deflected in dorsiflexion (FIG. 2) or plantarflexion (FIG. 3) as well as side to side (in FIG. 1 but not illustrated).

Referring to FIGS. 1–8, the implant has a metatarsal component 10 and a phalangeal component 12 which slide and move relative to each other along their convex and concave bearing surfaces 14, 16.

The metatarsal component has a head 18 which, on one side, defines the convex surface which terminates in a rear face 20, a portion 22 of which is angularly inclined relative to a line perpendicular to the rear face by an angle α of about 55° to define a flange 24 which extends the convex surface rearwardly past the rear face 20 as best seen in FIGS. 6 and 7. Flange 24 is located at the dorsal side of implant.

Figure 16:
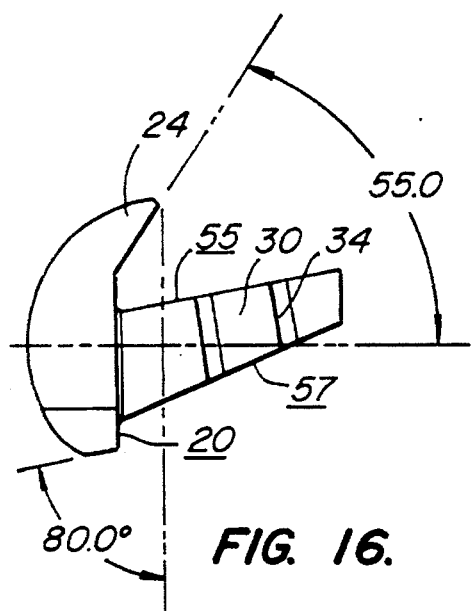
FIGS. 15–17 correspond to FIGS. 12–14 but illustrate a right foot metatarsal implant component constructed according to the present invention.
Figure 17:
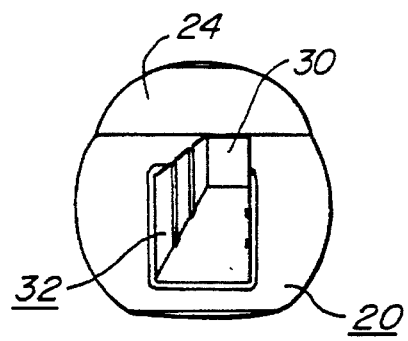

The convex surface 14 is spherically shaped except for a relatively small section 26 at the plantar side which has a slightly lesser radius (as indicated in FIG. 16) than the major part of the convex surface. Further, the plantar side of the head is truncated to define an end wall 28 which is inclined relative to the rear face 20 of the head by an angle β of about 80° to maintain the anatomic articulation of the sesamoids (shown in FIG. 18 only). FIG. 6 schematically illustrates the portion 26 of reduced curvature radius in the area where that portion slopes away from the circular phantom line of the circle defining the spherical curvature of the major portion of the convex surface. The reduced curvature portion 26 of the convex surface 14 lessens pressure on the underlying sesamoid and thereby enhances the comfort of the implant.

Figure 12:
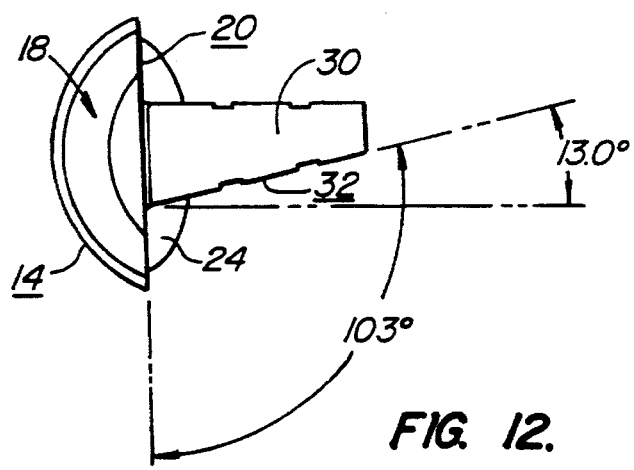
FIG. 12 is a detailed bottom end view of a left foot metatarsal implant component constructed in accordance with the present invention.
Figure 15:
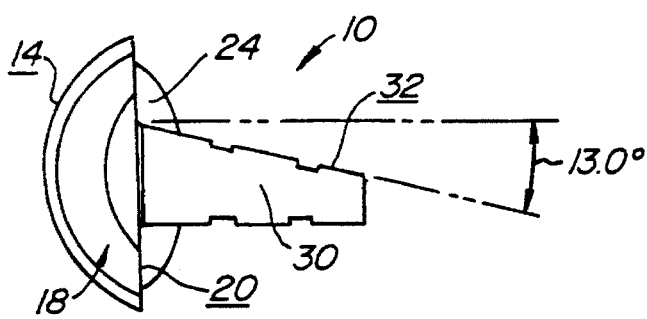

A stem 30 projects from the rear face 20 of the implant away from the convex surface 14, and it determines whether the metatarsal implant component 10 is intended for the right foot or the left foot. The stem has the shape of a longitudinally asymmetric, truncated pyramid and includes a side 32 inclined with respect to a line perpendicular to rear face 20 of the implant by about 13° (or inclined about 103° with respect to the rear face 20 as shown in FIG. 12). As FIGS. 12 and 15 illustrate, this side 32 is mirror-imaged on the left and right foot implants. By providing left and right foot implants, a relatively larger stem can be utilized so that a more secure and long-lasting stem-bone connection is obtained. Preferably, the stem includes surface grooves 34 which become filled with bone cement or, over time, will become filled with bone tissue to better anchor the stem.

Preparation of the metatarsal bone for the metatarsal implant component includes a 10° resection of the metatarsal head relative to the distal surface of the metatarsal, as is further discussed below. This minimizes the bony resection of the metatarsal head and leaves the plantar surface of the metatarsal head intact. The component is designed to sit at the 10° angle with the dorsal surface of the stem parallel to the axis of the metatarsal. By providing left and right foot implants, the stem optimally fits the shape of the medullary canal of the metatarsal bone.

Referring to FIGS. 1–11, the phalangeal component 12 includes a generally kidney-shaped base 36, a rear side 38 of which is placed against the resected phalangeal bone and from which a generally cylindrical stem 40 projects. The stem includes longitudinal grooves 42 (not shown in FIGS. 4 and 5) to prevent rotation of the stem, and therewith of the base, when it is implanted in the bone canal. Alternatively, stem 40 can be given a noncylindrical; e.g. a triangular, square, rectangular or other polygonal, cross-section (not shown). The stem may also include circumferential grooves 45 to facilitate the cementing of the implant and/or bony ingrowth into the grooves to provide a secure connection to the bone.

A generally cylindrical (in cross-section) insert 44 constructed of a relatively low-friction material such as polyethylene is nonmovably affixed to the side of the base opposite the stem so that the periphery of insert 44 is spaced inwardly from the periphery of the base. The insert includes a concavity 46 which is spherically shaped at a radius just slightly (e.g. in the order of 0.005 to 0.010 inches) larger than the radius of curvature of the main portion of convex surface 14 of the metatarsal implant to facilitate rotation and a slight translation of the convex metatarsal implant surface. By forming the cooperating convex and concave surfaces 14, 46 of the two implant components spherical, a full range of motion for the joint is assured. In addition, forces acting between the cooperating spherical surfaces are relatively evenly distributed over the surfaces to lower bearing pressures and thereby prevent undesirably high line pressures generated, for example, by implants having cooperating surfaces with differing surface configurations, as are encountered on some of the known implants mentioned above.

Figure 11:
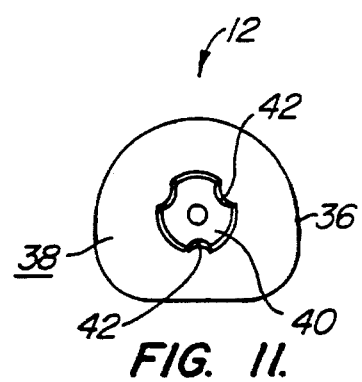
FIG. 11 is a rear elevational view of the phalangeal implant component.
Figure 13:
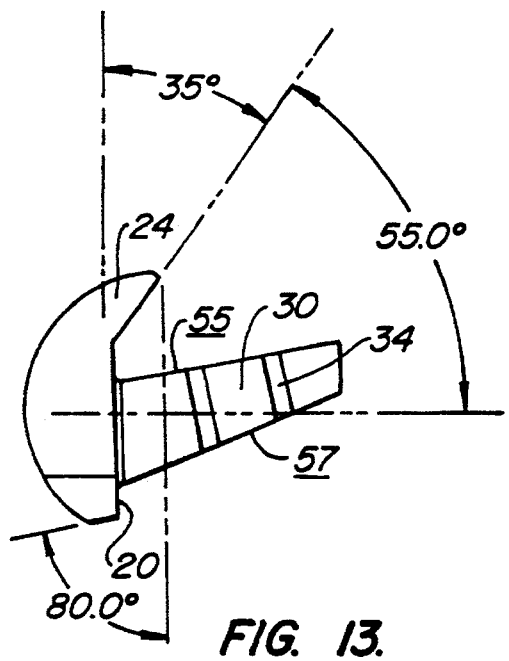
FIG. 13 is a side elevational view of the left foot metatarsal implant component shown in FIG. 12.
Figure 14:
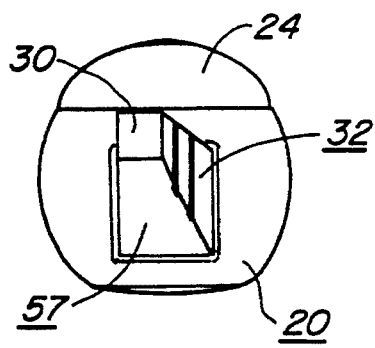
FIG. 14 is an end view of the left foot metatarsal implant component shown in FIG. 12.

Base 36 of the phalangeal implant is shaped so that its rear side 38 has substantially the same shape and size as resected phalangeal surface 60; e.g. it is somewhat kidney-shaped, as best seen in FIG. 11. By making the base of the implant component about the same size as the resected surface, the heretofore frequently encountered bone-overhang; i.e. the extension of the resected surface past the periphery of the implant base, is eliminated. Such an overhang, if present, can lead to bony overgrowth, which, in time, can interfere with the proper functioning of the implant. To avoid such a possibility on phalangeal implant components which have the heretofore more common cylindrical (round) base, the overhanging bone has sometimes been resected. Such resection is not only time consuming, it also involves an undesirable loss of bone structure and a resulting weakening of the phalangeal bone. This aspect of the present invention eliminates both.

The metatarsal component of the present invention can be made of any suitable material. However, cobalt chromium, a hard material which has good wear characteristics, is presently preferred. The phalangeal component is preferably made from medical-grade titanium alloy, for maximum bone apposition, and the insert is preferably made from ultra high molecular weight polyethylene (UHMWPE) to provide a bearing surface that is optimal for articulation with the cobalt chromium of the metatarsal component.

Further, it is preferred to provide a number of different sized components; e.g. three or four sizes, for both the metatarsal component and the phalangeal component to take into account different toe sizes. In addition, as discussed above, the metatarsal component is made in left and right configurations.

Turning now to the implantation of the implant of the present invention, a dorsal linear incision is initially made over the first metatarsal phalangeal joint parallel to the extensor hallucis longus tendon to expose and provide access to the metatarsal head and base. After the removal of any osteophytes from the dorsal surfaces of the proximal phalanx and distal metatarsal, the ends of the bones are resected.

Figure 18:
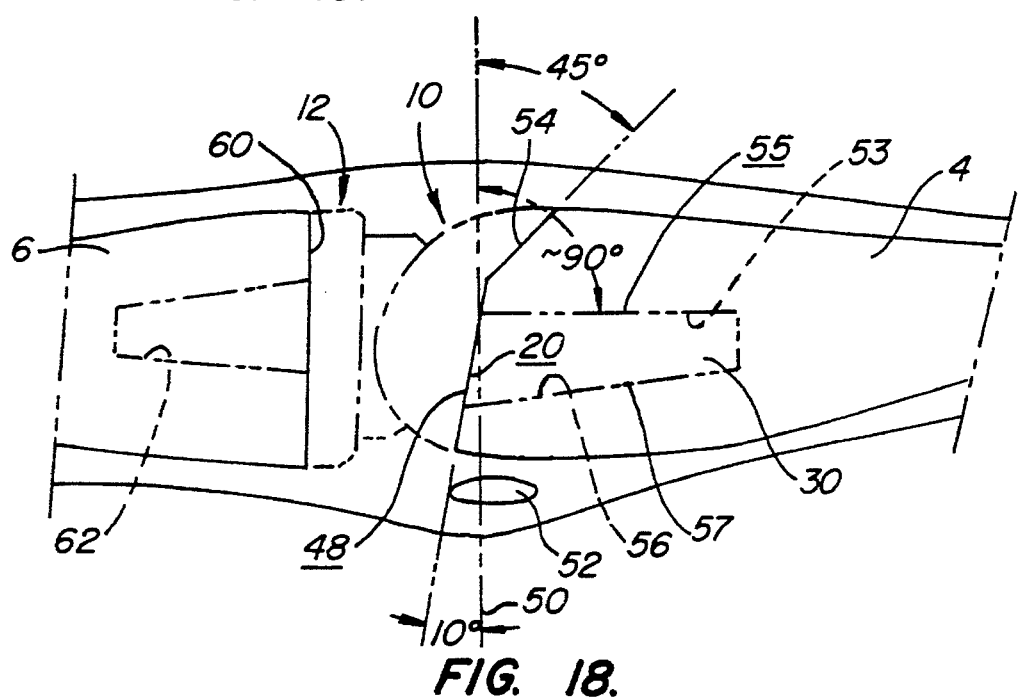
FIG. 18 is a schematic, side elevational view, not drawn to scale, which illustrates the implantation of the implant of the present invention between the metatarsal and phalangeal bones.

Referring particularly to FIG. 18 (not drawn to scale), the metatarsal bone 4 is resected to form a first resected surface 48 which is angularly inclined, preferably by about 10°, relative to a neutral cut or normal plane 50 which is perpendicular to the long axis of the bone and which typically intersects both the first resected plane 48 and the sesamoid 52 beneath the metatarsal bone. A further resected surface 54 is formed on the metatarsal bone which is angularly inclined relative to normal plane 50 by about 45° or 35° relative to rear face 20, and which is sized and shaped so that rear face 20 and portion 22 thereof abut against resected surfaces 48, 54, respectively, upon the implantation of the implant.

Next the medullary canal (not separately shown in the drawings) is broached out to define interior bone surfaces that engage stem 30 of the metatarsal implant. To do so, the bone is broached to define an interior surface 53 on the dorsal side of the canal for engaging a dorsally facing stem surface 55 that is substantially perpendicular to normal plane 50 and, therefore, angularly inclined relative to rear face 20 by about 80°. The medullary canal of the metatarsal bone is broached so that it additionally defines a surface 56 on the plantar side of the canal which has the same angularity as stem surface 57 on the plantar side thereof; i.e. an angle of 103° relative to the rear face 22 of the implant.

The phalangeal bone is resected to define a resected surface 60 which is generally perpendicular to the floor, and therefore parallel to normal plane 50, so that the rear side 38 of the phalangeal implant 12 can abut it when implanted. Further, the phalangeal bone is appropriately broached to form a cavity 62 therein into which the stem 40 of the phalangeal implant fits snugly.

Following resection, the implant components are implanted by pushing and tapping the stem of each component into the bone cavity until rear faces 20, 22 of the metatarsal implant and rear side 38 of the phalangeal implant abut the respective resected surfaces 48, 54 and 60. The implants are conventionally secured to the bone in any desirable manner such as with cement, frictionally and/or by way of bony ingrowth.

It will be noted that the 10° inclination of rear face 22 relative to normal plane 50 and the rearwardly extending flange 24 of the metatarsal implant provide a number of advantages. First, the 10° angular inclination of the rear face of the metatarsal implant, coupled with the geometry of the stem as described above so that it is effectively aligned with the medullary canal of the metatarsal bone, rotate the metatarsal implant upwardly (dorsally) and, in conjunction with flange 24 and the rearwardly extended concave surface 16 formed by it, extend the range of dorsiflexion of the implant, where a maximum range of motion is needed, by about 45°. This is particularly important because the implant is subjected to maximum forces during toe-off. At the same time, the stem of the metatarsal implant component is oriented so that it follows the inclination of the metatarsal bone.

Still further, the 10° inclination of the rear face of the metatarsal component limits the amount of bone that must be resected and rotates its plantarly facing end away from the underlying sesamoidal bone. As a result, except during plantar flexion, which occurs relatively less frequently and during which the joint is normally not heavily stressed, the natural metatarsal bone overlies the sesamoid and need not be resected to properly receive the metatarsal implant component, which enhances the performance of the implant.

What is claimed is:

1. A prosthetic great toe implant between a patient's metatarsal and phalangeal bones and overlying a sesamoid bone of the patient, the prosthetic implant comprising a first component defining a partially spherical, convex surface terminating at a rear face of the component and a stem projecting from the rear face into a cavity of the metatarsal bone, the rear face is inclined about 10° with respect to a normal plane, the normal plane is perpendicular to a long axis of the metatarsal bone, and the rear face abuts against a resected surface; and a second implant component including a base with a rear side abutting a resected surface of the phalangeal bone, a stem projecting from the rear side into a cavity in the phalangeal bone, and an insert defining a partially spherical convex surface slidably engaging the concave surface of the first implant to permit articulation between the metatarsal and phalangeal bones along the spherical surfaces.

2. A prosthetic implant according to claim 1 wherein the stem projecting from the rear face of the first implant component includes a side facing in a dorsal direction and extending over at least a portion of a length of the stem, the stem side being angularly inclined relative to the rear face by about 80°.

3. A prosthetic implant according to claim 1 wherein the first component includes a flange extending from the rear face towards the phalangeal bone and defining a continuation of the spherical, convex surface beyond the rear face.

4. A method for implanting a prosthetic great toe implant between a patient's metatarsal and phalangeal bones, the method comprising the steps of providing a first implant component defining a partially spherical, convex surface terminating at a rear face of the component, the rear face is inclined about 10° with respect to a normal plane, the normal plane is perpendicular to a long axis of the metatarsal bone, and a stem projecting from the rear face for placement in a cavity of the metatarsal bone;

providing a second implant component including a base with a rear side and a stem projecting therefrom for placement in a cavity of the phalangeal bone, and an insert defining a partially spherical concave surface for movably engaging and cooperating with the convex surface upon implantation of the components;

resecting the metatarsal bone to form a surface which is angularly inclined by about 10° relative to a normal plane;

resecting the phalangeal bone to form a second resected surface;

implanting the first and second components by extending their stems into the respective bone cavities so that the rear face of the first component abuts the first resected surface and the rear side of the second component abuts the second resected surface; and securing the first and second components to the metatarsal bone and the phalangeal bone, respectively.

5. A method according to claim 4 wherein the normal plane intersects the resected surface.

6. A method according to claim 4 including the step of providing the first component with a flange extending from the rear surface in the direction of the metatarsal bone and defining a continuation of the spherical surface beyond the rear face; and resecting a third surface on the metatarsal bone which is contiguous with the first resected surface, which defines an angle relative to the normal plane which is greater than the angle between the first resected surface and the normal plane, and which is shaped and positioned so that the flange abuts the third surface.

7. A method according to claim 4 wherein the stem projecting from the rear face of the first component includes a surface facing in a dorsal direction which defines an angle relative to the rear face which is substantially the same as the angle between the rear face and the normal plane so that the stem surface facing in the dorsal direction is at substantially 90° with respect to the normal plane, and including the step of broaching the medullary canal so that it forms a surface complementary to the surface of the stem facing in the dorsal direction.

8. A method according to claim 7 including the step of forming on the stem projecting from the rear face a surface facing in a dorsal direction which forms an angle relative to the rear face of about 55°, and including the step of broaching the medullary canal in the metatarsal bone to form a surface therein which corresponds in shape and orientation to the surface on the stem facing in a dorsal direction.

* * * * *